United States Patent
Harvie (10) Patent No.: US 7,202,852 B2
(45) Date of Patent: Apr. 10, 2007

(54) ACTIVE LASER PROTECTION SYSTEM

(76) Inventor: Mark R. Harvie, 1150 Airport Dr., South Burlington, VT (US) 05403

( * ) Notice: Subject to any disclaimer, the term of this patent is extended or adjusted under 35 U.S.C. 154(b) by 331 days.

(21) Appl. No.: 11/031,305

(22) Filed: Jan. 7, 2005

(65) Prior Publication Data

US 2005/0162575 A1  Jul. 28, 2005

(51) Int. Cl.
*G09G 5/08* (2006.01)
*G09G 5/00* (2006.01)

(52) U.S. Cl. .............................. 345/158; 345/7; 345/8; 345/165; 345/166

(58) Field of Classification Search ............... 345/7–9, 345/156–166, 173–178, 11–15, 59; 359/13, 359/465, 630–635
See application file for complete search history.

(56) References Cited

U.S. PATENT DOCUMENTS 4,792,697 A * 12/1988 Le Parquier et al. .... 250/559.3
4,879,167 A * 11/1989 Chang ........................ 428/215
5,914,661 A * 6/1999 Gross ......................... 340/600
7,126,583 B1 * 10/2006 Breed ......................... 345/158

* cited by examiner

*Primary Examiner*—Vijay Shankar
(74) *Attorney, Agent, or Firm*—Eric R. Benson

(57) ABSTRACT

This invention relates to an active Laser Protection System (LPS) system specifically designed to provide a device that automatically adjusts a protection panel of the device in response to laser light exposure thus preventing a user from being exposed to damaging laser light. In one embodiment the LPS system utilizes a light weight portable goggle type eyewear. In yet another embodiment the LPS system is comprised of contact lenses worn by the user. The LPS system may be used in all light transmissive surfaces where the penetration of laser light is not desired, such as aircraft, spacecraft, vessel, train, and automotive windshields, etc. The LPS system may also be utilized as a replacement window for structures where laser light penetration is undesired. The protection panels utilize Liquid Crystal Displays (LCD) that are activated by laser sensors by means of a microprocessor and power supply means. The device also automatically replaces non-laser visible light that may be blocked because the light was of the same wavelength as the blocked light by projecting that light by means of activating the LCD accordingly by means of the microprocessor.

17 Claims, 5 Drawing Sheets

ACTIVE LASER PROTECTION SYSTEM

BACKGROUND ART

Almost immediately upon the invention of laser technology there has been a long felt need for effective laser protection system (LPS). Exposure to laser light can cause significant and sometimes permanent damage to persons and property depending upon the type of laser, the length of exposure and the intensity of the laser. For example, the parts of the eye which are of most serious concern in laser exposure hazards to the eye are the cornea, lens, pupil/iris, and retina.

There are three major mechanisms by which living tissue can be damaged by laser light which are thermal, acoustic, and photochemical. Thermal effects are the major cause of eye tissue damage by lasers. Energy from the laser is absorbed by the eye tissue in the form of heat which often causes localized intensive heating of sensitive eye tissues. The amount of thermal damage varies depending on the thermal sensitivity of the type of eye tissue. The thermal effects of laser exposure can range from erythema to an actual burning of the eye tissue. The main factors affecting thermal damage to eye tissue are the amount of the eye tissue exposed, the wavelength of laser light, the energy of the laser beam, and the length of time that the tissue is irradiated by the laser.

Laser beams are also capable of causing a localized vaporization of eye tissue which in turn can create a mechanical shockwave that is in turn propagated through the remaining eye tissue. These shockwaves can cause significant tearing of eye tissues. Lastly, laser light can also cause significant changes to the chemistry of cells in the eye, which can result in changes to eye tissue that impair or even destroy the vision of the eye.

The wavelengths of laser light that are of particular concern in the development of LPS are the portion of the electromagnetic (EM) spectrum known as the optical portion of the spectrum, which consists of the infrared (IR) (780 nm–1 mm), ultraviolet (UV) (200–400 nm) and also the visible portions of the EM spectrum wavelengths (400–780 nm) between them.

Early developed lasers operated predominantly at only two wavelengths making the development of LPS relatively simple. For instance, U.S. Pat. No. 4,601,533, Laser Eye Protection Visor Using Multiple Holograms (Moss 1986) teaches LPS protection for the then known laser wavelengths by use of holographic fringes. In this prior art each of the holograms has a predetermined fringe spacing designed to reflect a given wavelength. The angle of peak diffraction efficiency of one of the holograms in this patent is designed to always coincide with the line of sight to the eye in question. This prior art utilization of two holograms to reflect radiation of a given wavelength produce a system providing sufficient angular bandwidth suitable for wide angular coverage which was sufficient for that time.

However, the number of wavelengths of lasers that are now being used either militarily or commercially is proliferating. It is a matter of public knowledge that tunable or frequency agile lasers are currently being developed, having there most significant threat in military uses, and for which there is no suitable LPS. The present state of the art LPSs are based on narrow band spectral line rejection filters at the threat laser wavelengths, attenuating incident laser energy at these wavelengths and thus preventing laser radiation from injuring or killing and/or destroying property.

More recent developments of LPS systems such as U.S. Pat. No. 5,116,113 (Chu, 1992) teach laser eye protective devices using metal ion-containing polymers. Other efforts at manufacturing effective LPSs that are commercially available existing art are a combination of optical thin film coating technologies and absorbing dyes that are designed to protect the user from lasers in the infrared and visible portions of the electromagnetic spectrum. Leading research engineers in the industry are currently working to improve the transmission characteristics of laser-absorbing dyes, to evaluate the reflective (dielectric stack, holographic mirrors, and rugate filters) and hybrid technologies, and enhance LPS scratch resistance polycarbonate hard-coating technologies. This technology deposits wavelength specific filters on spectacles, goggles, and visors to prevent non-visible laser energy from damaging eyes. The addition of advanced filters (either holographic or rugate) can block visible laser energy, while allowing other visible light to pass unimpeded.

The technical approach of the prior art LPSs used to protect against fixed frequency lasers cannot be applied to protection from the agile or variable laser or even to protection from a larger number of fixed frequency lasers currently in use. Prior to the disclosed invention the only known way to protect from multiple wavelengths of lasers is to stack or sandwich multiple layers of these advanced filters. As more band rejection filters are built into a sandwich, however, transmissivity of the LPS at other wavelengths decreases also, making it unusable at night and severely limiting its utility in the daytime. It is well known in the prior art that the level of attenuation provided by prior art LPSs at present laser wavelengths are generally only adequate against lower powered lasers which are increasingly being used as military weapons.

The United States Homeland Security Agency and related U.S. government agencies have been concerned that commercial, as well as military, aircraft are both a prime target for laser weapon useage, primarily to induce flash blindness. The penetration of laser light into the cockpit of an aircraft, or vehicle of any sort, can temporarily, and if powerful enough, permanently blind the pilot or operator. This could have disastrous results. Recent news accounts in the U.S. of laser penetration into the cockpits of commercial aircraft has intensified the need to have some manner of protection from these very serious threats.

Laser sensors are well known and commercially available. The use of these laser sensors as part of laser protection has been taught and involves the use of sensors as part of a laser protection program. The sensors in the prior art provide laser illumination sensing and analysis capability prior to the exposure of the person being warned. In theory the time gained can be used by the person to take reflexive protection measures and engage in laser illumination evasion, which most often meant putting on the proper wavelength(s) LPS. Insofar as laser light travels at the speed of light, it is easy to recognize the inadequacy of this system which requires first deciding which LPS device is needed and then physically having to put the device on.

A review of prior and current LPS technologies reveal that there are no acceptable prior art active laser protection systems that protect against all laser light in one device. Also, there are no automatic or active LPS devices known in the prior art. The prior art reveals that the known LPS technology uses passive systems that are inadequate for the rapidly evolving laser weapon industry. Because the prior art has been limited to the use of laser-absorbing dyes, reflective (dielectric stack, holographic mirrors, and rugate filters) and hybrid technologies, the inherent limitations of these systems make it difficult, if not impossible, to protect a user from all the possible laser wavelengths, or do so automatically.

Furthermore, there is no prior art LPS devices that utilize laser detection to both automatically adapt the laser blocking aspect of the device as well as automatically display critical data regarding the number, nature (i.e. wavelength) and direction of one or more intruding laser beams. These features coupled with real time holographic projection of the visible spectrum to replace the non-laser blocked light that happens to be blocked because it is the same wavelength as the blocked laser is another feature not found in the prior art.

While each of these prior art LPS devices fulfill their respective particular objectives and requirements, and are most likely quite functional for their intended purposes, it will be noticed that none of the prior art cited disclose an apparatus and/or method that is automatic, portable, rugged, and lightweight and that can provide laser protection from all wavelengths of laser light.

As such, there apparently still exists the need for a new and improved active laser protection system to maximize the benefits to the user and minimize the risks of injury from its use.

In this respect, the present invention disclosed herein substantially corrects these problems and fulfills the need for such a device.

DISCLOSURE OF THE INVENTION

In view of the foregoing limitations inherent in the known types of Laser Protection Systems (LPS) now present in the prior art, the present invention provides an apparatus that has been designed to provide the following features for a user:

- The system may be used in a lightweight, one piece eyewear that may be curved or contoured to maximize laser light protection and minimize the weight of the device or even as contact lenses
- Durable and able to withstand shrapnel impact, ejection windblasts, environmental stresses (extreme temperatures, solar radiation), and scratching caused by operational use
- The system may be used wherever a transparent or translucent surface is desired, such as a window of a structure, the windshield of an aircraft, spacecraft, or ground vehicle, etc.
- Automatically electronically Microprocessor controlled
- Equipped with Laser Sensors
- Provides eye protection for the laser wavelength(s) to which the user is actually exposed
- Utilizes transmissive liquid crystal displays (LCD)
- Resistant to chemical agents
- Easy to maintain
- Produces non-visual field interfering holographic display of user needed information, i.e. laser source direction, laser intensity, laser wavelength and LPS efficacy
- Automatically replaces non-laser light to the visual field on the protected or user side of the LPS to replace the non-laser light that is blocked as a direct result of the blocking of laser light of the same wavelength These features are improvements which are patently distinct over similar devices and methods which may already be patented or commercially available. As such, the general purpose of the present invention, which will be described subsequently in greater detail, is to provide a field designed apparatus and method of use that incorporates the present invention. There are many additional novel features directed to solving problems not addressed in the prior art.

To attain this the present invention generally comprises four major components: 1) an LPS Frame (in the eyewear and window/windshield embodiments); 2) one or more color Liquid Crystal Display (LCD) Panels sandwiched between Protective Lenses mounted in the LPS Frame; 3) one or more Laser Sensors electronically connected to; 4) a Power Supply and Microprocessor that translates the input it receives from the Laser Sensors and correspondingly activates one or more of the LCD Panels in response thereto.

An additional object and advantage of the present invention is that unlike the prior art LPS devices the present invention does not require any action on the part of the user in response to exposure to laser light, the present invention senses the wavelength and strength of a laser to which the user has become exposed and automatically activates LCD color panels to block the transmission of harmful laser light into the eye of the user without completely blocking the user's sight through the device, maintaining visual acuity of the user. This visual acuity is maintained in two important ways. First, only the wavelength of light representing the offensive laser light is blocked and then the resultant blocked non-laser light of the same wavelength is replaced holographically, in essence maintaining full light spectrum viewing. This aspect is especially critical in the event that the LPS is assaulted with multiple differing wavelengths of laser light, which when all blocked by the LPS would in essence block all corresponding non-laser visible light causing the LPS to go dark, blocking vision completely.

Additionally the present invention's microprocessor can project on the LCD a holographic non-sight impairing text message that will alert the user to the type and strength of the laser to which the user is then exposed as well as the direction from which the laser is coming. Another advantage of the eyewear embodiment of the present invention is that the protective lenses (by use of glasses or contacts) can be made to correct the vision of a user, such that a user that ordinarily wears glasses or contacts to correct a vision problem will not have to wear their glasses with this invention, it correcting the impairment as if the glasses or contacts were being worn.

These together with other objects of the invention, along with the various features of novelty which characterize the invention, will be pointed out with particularity in the claims which are annexed hereto and forming a part of this application. For a better understanding of the invention, its operating advantages and the specific objects attained by its uses, reference should be had to the accompanying drawings and descriptive matter in which there is illustrated preferred embodiments of the invention.

BEST MODES FOR CARRYING OUT THE INVENTION

I. Preferred Embodiments

A. Eyewear Embodiment

With reference now to the drawings, and in particular to FIGS. 1–5 thereof, a new and novel Laser Protection System (LPS) device embodying the principles and concepts of the present invention is depicted in these drawings as comprising four major components: 1) an LPS Frame (7); 2) one or more color Liquid Crystal Display (LCD) Panels (2A,2B, 2C,2D,10A,10B,10C) sandwiched between Protective Lenses (4,4A,6,6A) mounted in the LPS Frame (7); 3) one or more Laser Sensors (8) electronically connected to; 4) a Power Supply and Microprocessor (9) that translates the input it receives from the Laser Sensors (8) and correspondingly activates one or more of the LCD Panels (2A,2B,2C, 2D,10A,10B,10C) in response thereto, and the Active Laser Protection System Goggles are generally designated by the reference numeral (1).

B. Contact Lens Embodiment

Figure 1:
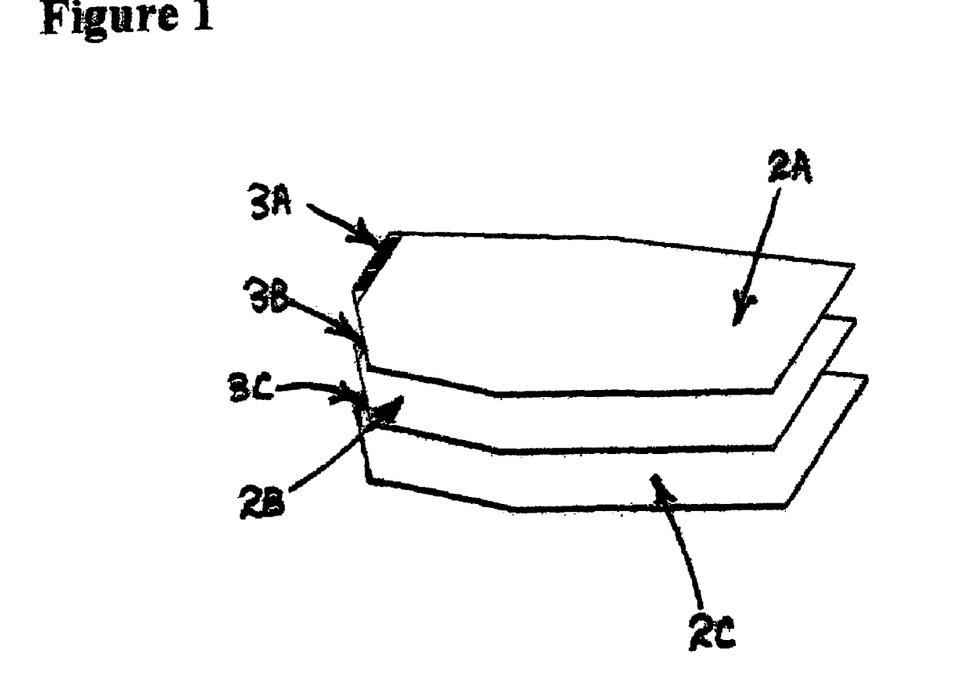
FIG. 1 is an exploded perspective view of the three color embodiment placement of the Liquid Crystal Displays (LCD).
Figure 2:
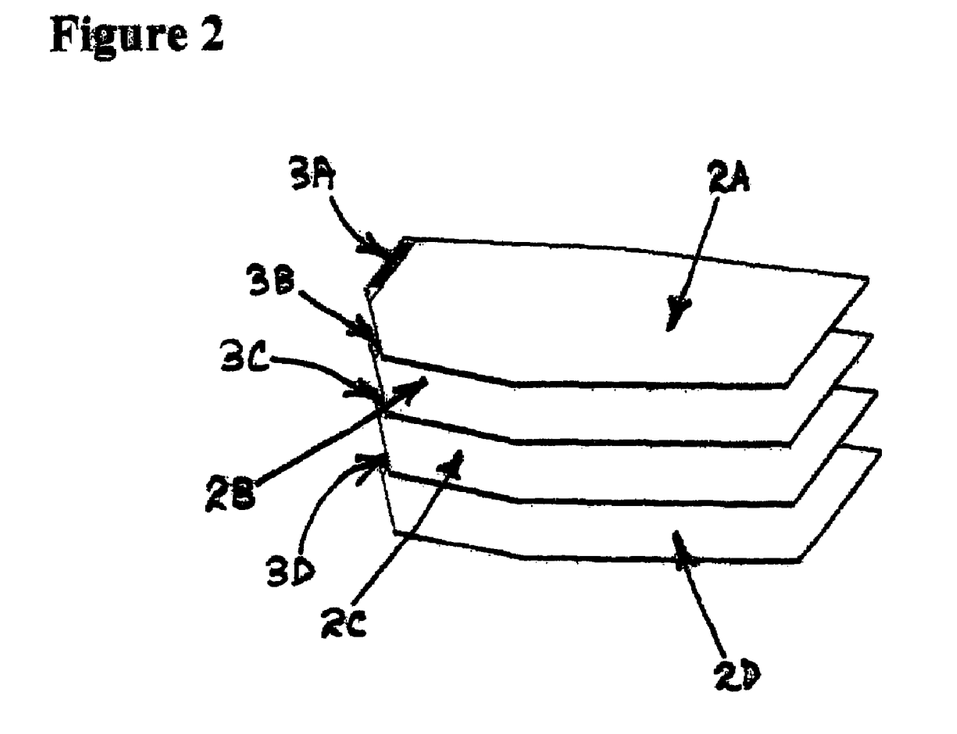
FIG. 2 is an exploded perspective view of the four color embodiment placement of the Liquid Crystal Displays (LCD).
Figure 3:
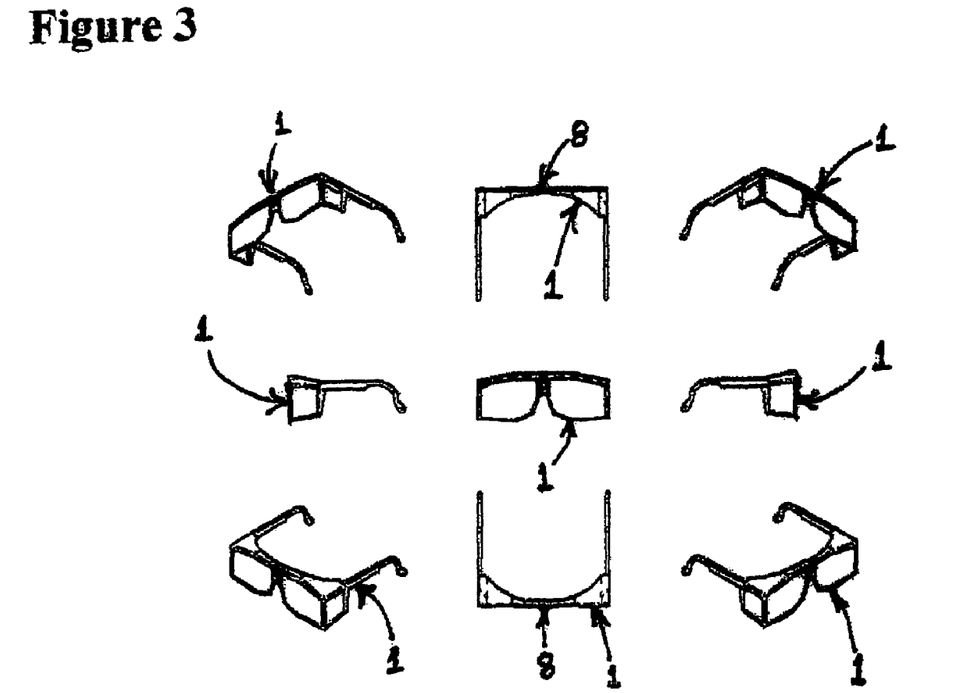
FIG. 3 depicts nine perspective views of the Eyewear Embodiment of the Laser Protection System (LPS) device.
Figure 4:
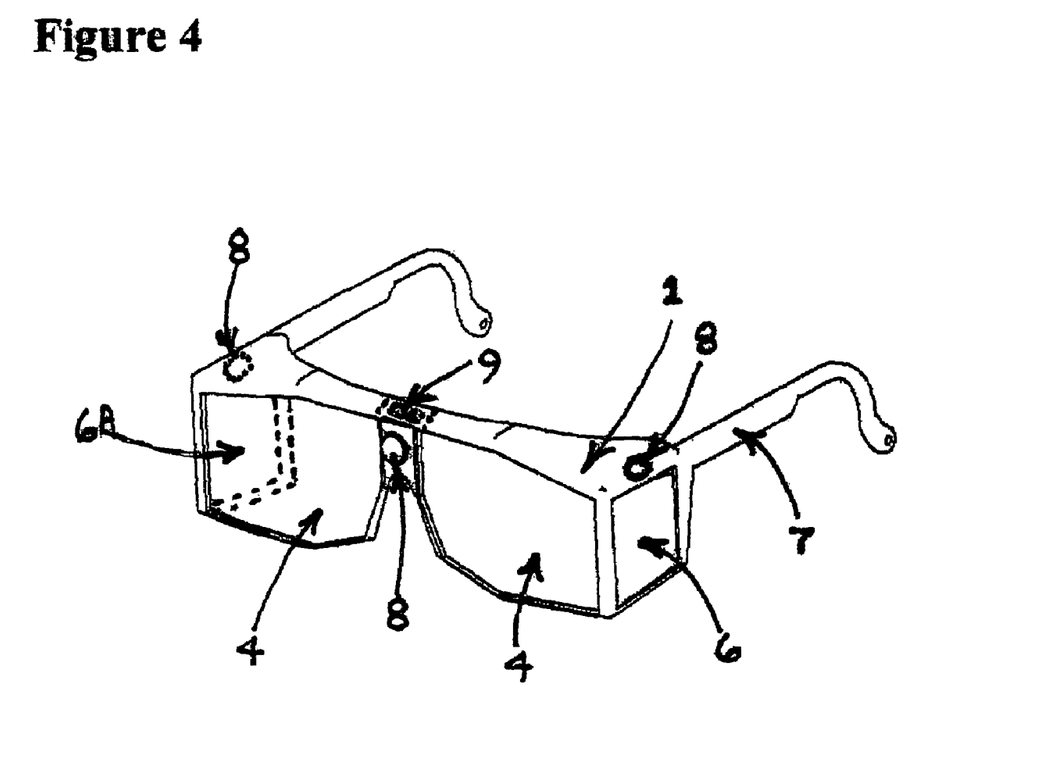
FIG. 4 is a perspective view of the Eyewear Embodiment of the Laser Protection System (LPS) device.
Figure 5:
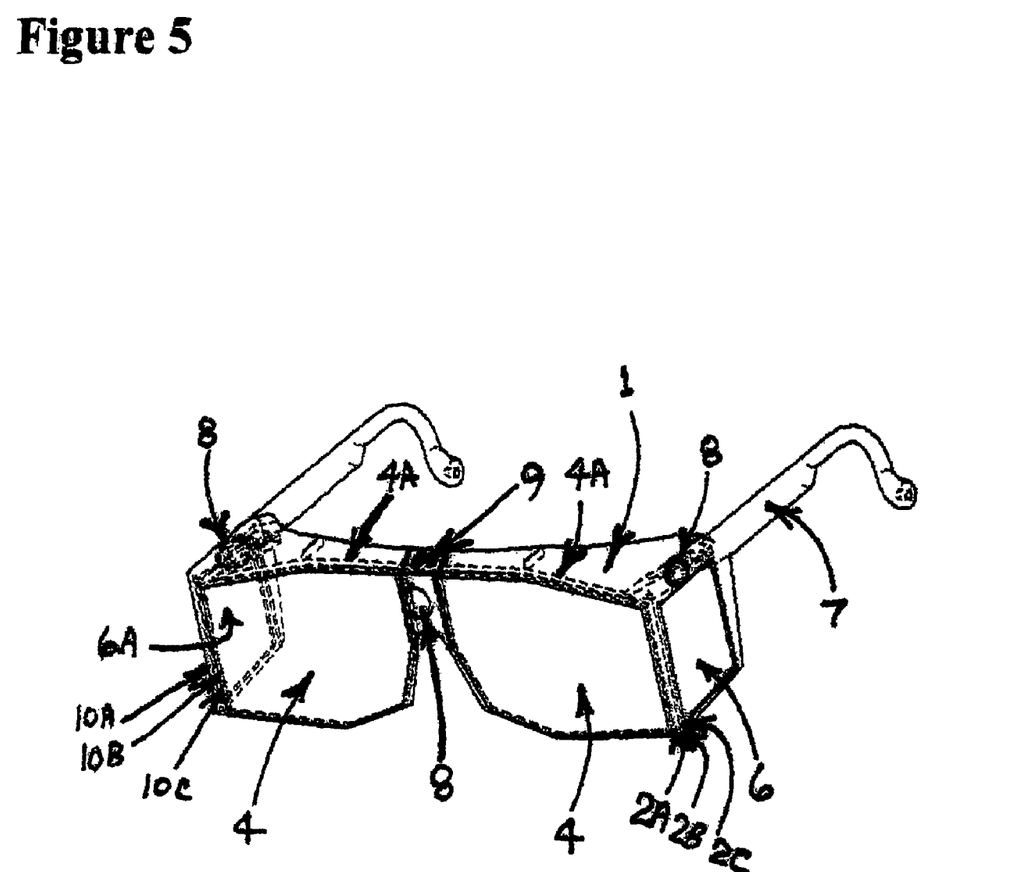
FIG. 5 is a perspective view of the Eyewear Embodiment of the Laser Protection System (LPS) device further depicting concealed features with hatched lines.
Figure 6:
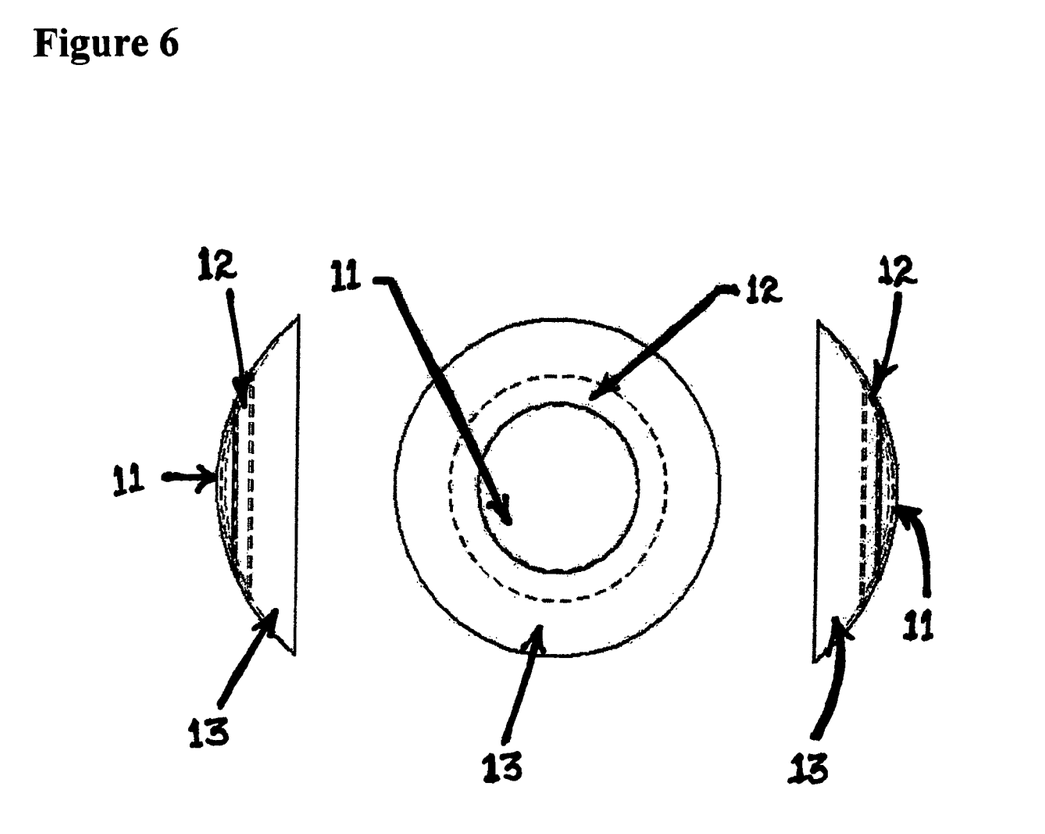
FIG. 6 is a perspective front and two perspective side views of the contact lens embodiment of the Laser Protection System (LPS).

With reference now to the drawings, and in particular to FIG. 6 thereof, a new and novel Laser Protection System (LPS) device embodying the principles and concepts of the present invention is depicted in this drawing as comprising three major components: 1) a Contact Lens Imbedded LCD Panel (11); 2) an Imbedded Laser Sensor Power Supply and Microprocessor (12) disposed around and in electronic communication with the Contact Lens Imbedded LCD Panel (11); and 3) a Contact Lens Outer Rim (13) to hold the device in place on the user's eye.

C. Window/Windshield Embodiment

Figure 7:
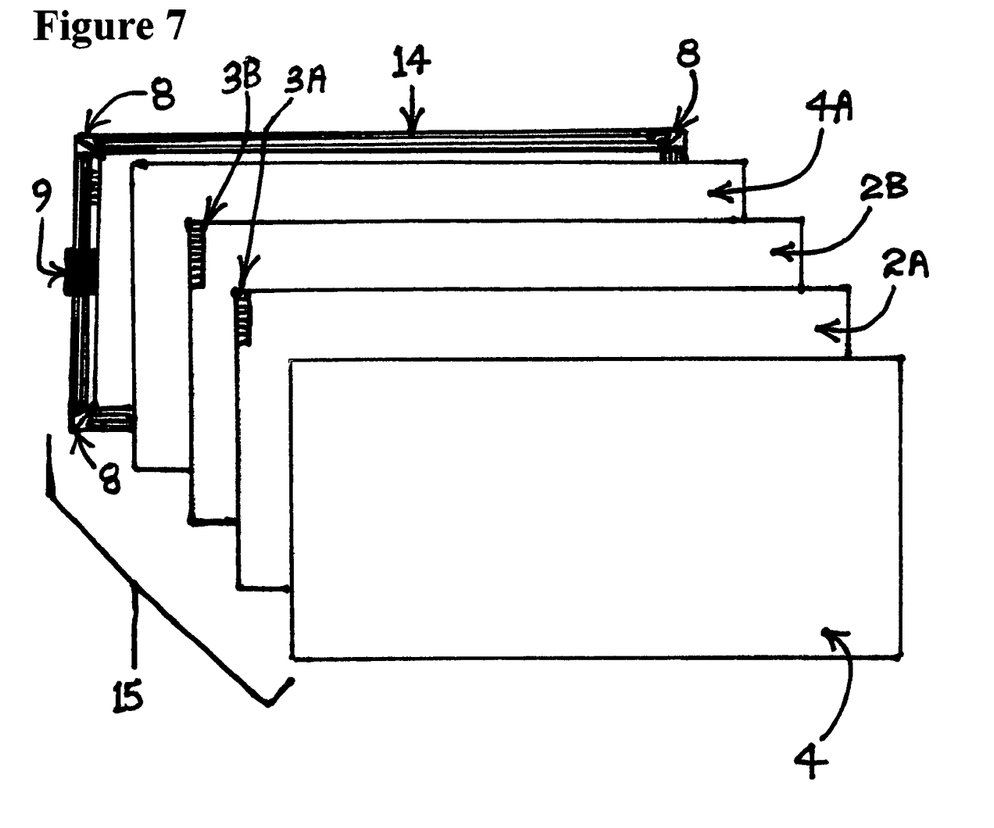
FIG. 7 is an exploded perspective view of the window/windshield embodiment of the Laser Protection System (LPS).

With reference now to the drawings, and in particular to FIG. 7 thereof, a new and novel Laser Protection System (LPS) device embodying the principles and concepts of the present invention is depicted in this drawing as comprising four major components: 1) a Window/Windshield LPS Frame (14); 2) one or more color Liquid Crystal Display (LCD) Panels (2A,2B) sandwiched between Protective Lenses (4,4A) mounted in the Window/Windshield LPS Frame (14); 3) one or more Laser Sensors (8) electronically connected to; 4) a Power Supply and Microprocessor (9) that translates the input it receives from the Laser Sensors (8) and correspondingly activates one or more of the LCD Panels (2A,2B) through the LCD Panel Electronic Interfaces (3A, 3B) in response thereto, and the Active Laser Protection System Window/Windshield is generally designated by the reference numeral (15).

General Description of Reference Numerals in the Description and Drawings

Any actual dimensions listed are those of the preferred embodiments. Actual dimensions or exact hardware details and means may vary in a final product or most preferred embodiment and should be considered means for so as not to narrow the claims of the patent.

List and Description of Component Parts of the Invention:

| | |
|---|---|
| (1) | Active Laser Protection System Goggles |
| (2A) | Color 1 LCD Panel |
| (2B) | Color 2 LCD Panel |
| (2C) | Color 3 LCD Panel |
| (2D) | Color 4 LCD Panel |
| (3A) | Color 1 LCD Panel Electronic Interface |
| (3B) | Color 2 LCD Panel Electronic Interface |
| (3C) | Color 3 LCD Panel Electronic Interface |
| (3D) | Color 4 LCD Panel Electronic Interface |
| (4) | Outside LCD Protective Lens |
| (4A) | Inside LCD Protective Lens |
| (6) | Side Panel Outside LCD Protective Lens |
| (6A) | Side Panel Inside LCD Protective Lens |
| (7) | LPS Frame |
| (8) | Laser Sensor |
| (9) | Power Supply and Microprocessor |
| (10A) | Side Color 1 LCD Panel |
| (10B) | Side Color 2 LCD Panel |
| (10C) | Side Color 3 LCD Panel |
| (11) | Contact Lens Imbedded LCD Panel |
| (12) | Imbedded Laser Sensor Power Supply Microprocessor |
| (13) | Contact Lens Outer Rim |
| (14) | Window/Windshield LPS Frame |
| (15) | Active Laser Protection Window/Windshield |

Detailed Description of the Preferred Embodiments:

The most preferred embodiment of the Active Laser Protection System Goggles (1) depicted in FIGS. 1–5 is comprised of the following components in their respective functional relationships:

The invention accomplishes its intended purpose of protecting a user's eyes by means of one or more Liquid Crystal Displays (LCD) of various color or wavelength capabilities (2A,2B,2C,2D,10A,10B,10C). The LCDs selected are transmissive allowing visual spectrum light to pass through and can be selected from the current technologies available which are either twisted nematic displays, super twisted nematic displays or bistable nematic displays. Any LCD commercially available or future developed will be suitable for use in this invention so long as the LCD is transmissive and can provide specific wavelength displays capable of complete occlusion of laser light of the said wavelength. The various color LCDs (2A,2B,2C,2D) of the four color embodiment are each sandwiched between an Outside LCD Protective Lens (4) and an Inside LCD Protective Lens (4A) all of which are in turn rigidly mounted in the LPS Frame (7). Similarly as depicted in the three color embodiment the various side panel LCDs (10A,10B,10C) each is sandwiched between a Side Panel Outside LCD Protective Lens (6) and a Side Panel Inside LCD Protective Lens (6A) all of which are in turn rigidly mounted in the LPS Frame (7).

An array of Laser Sensors (8) are attached to the LPS Frame (7) to detect the presence of laser light from any possible direction that may enter the eyes of a user. If one or more Laser Sensors (8) detects the presence of laser light it communicates this information to the Microprocessor and Power Supply (9) which in turn translates this information and correspondingly activates one or more of the LCD panels (2A,2B,2C,2D,10A,10B,10C) through its electronic connection to the various color LCD Panel Electronic Interfaces (3A,3B,3C,3D) such that the activated LCD Panels will block the transmission through the LCD Panels of any laser light, such that only the wavelengths of light corresponding to the laser will be blocked and the remainder of the visual spectrum will still be permitted to pass therethrough, thus not blocking the vision of a user whose eyes are being protected from the laser light. The various Side Color LCD Panel Electronic Interfaces are not shown in the Figures, but are identical in form and function to the color LCD Panel Electronic Interfaces (3A,3B,3C,3D). In yet another embodiment of the present invention, the array of Laser Sensors (8) that are attached to the LPS Frame (7) to detect the presence of laser light from any possible direction that may enter the eyes of a user also senses the strength, type and direction of any laser light to which it is exposed. Then the Laser Sensors (8) communicate this information to the Microprocessor and Power Supply (9) which in turn translates this information and not only does it correspondingly activate one or more of the LCD panels (2A,2B,2C, 2D,10A,10B,10C) to block the transmission through the LCD of the laser light as described above, it also generates a holographic type text message to the user providing the user with information such as the type of laser to which the user is being exposed as well as its strength and perhaps more importantly the direction from which the laser is coming, in order that the user may take evasive measures. In the most preferred embodiments of all embodiments of the LPS the blocked visible light (blocked because it is of the same wavelength as the blocked laser light) is replaced. The Microprocessor and Power Supply (9) sense the visual field that has been blocked because of the offending laser and projects whatever light or image (or part thereof) that has been blocked onto one or more of the LCD panels (2A,2B, 2C,2D,10A,10B,10C). This light or image replacement capacity is a failsafe in the event that the wavelengths of visual light that may be blocked will not cause the device to "go dark" preventing any vision. The device being capable of generating a spatially correct LCD displayed real time image of the user's visual field automatically for part or all of any blocked light that may result from blocking corresponding wavelengths of laser light.

The Contact Lens Embodiment depicted in FIG. 6 and the Window/Windshield Embodiment depicted in FIG. 7 function in the same manner as the Eyewear Embodiment listed above. Each embodiment utilizes a laser detection means, a microprocessor to interpret the laser detection signal, one or more LCD panels that are activated in response to the interpreted data and some means of holding the LCD panels in place for use.

While my above descriptions of the invention, its parts, and operations contains many specificities, these should not be construed as limitations on the scope of the invention, but rather as exemplifications of present embodiments thereof. Many other variations are possible, for example, other embodiments, shapes, and sizes of the device can be constructed to fit into the windows of a vehicle, aircraft, building or any other interface between a user and a laser light source and designed to work by the principles of the present invention; various materials, colors and configurations can be employed in the device's design that would provide interesting embodiment differences to users including such practical designs as would, for instance provide wireless communication to the microprocessor from various external sources some distance apart from the user. The LPS device may also be constructed of bicarbonate materials with the LCD Panels molded inside. The Power Supply may also be photovoltaic, as well as many other obvious variations.

It would also be considered obvious that the LCD Panels comprising the lenses of the device may also be curved or contoured in shape to maximize eye protection, and prevent frame type visual field obstruction typical with many safety goggle type configurations. These contoured LCD Panels can be cast into a polycarbonate frame structure which further minimizes visual field obstruction while maintaing lightweight design.

Accordingly, the scope of the invention should be determined not by the embodiments illustrated, but by the claims and their legal equivalents.

The invention claimed is:

1. An active Laser Protection System device comprising:
    at least one laser detection means;
    at least one microprocessor;
    at least one liquid crystal display;
    the liquid crystal display is further comprised of a laser exposed side and a user side:
    at least one laser detection communication means in electronic communication with the laser detection means and the microprocessor such that when the laser detection means detects a laser light the laser detection communication means, then communicates all available data regarding the laser light from the laser detection means to the microprocessor and then the microprocessor processes the data being communicated from the laser detection means; at least one liquid crystal display communication means in electronic communication with the microprocessor and the liquid crystal such that when the laser detection means detects a laser light and the microprocessor has processed the data from the laser detection means, the microprocessor activates the liquid crystal display in response thereto by communicating with the liquid crystal display by means of the liquid crystal display communication means; and
    the microprocessor causes the liquid crystal display to display on the user side any visible non-laser light that was prevented from passing from the laser exposed side to the user side of the same wavelength as the laser light that was prevented from passing from the laser exposed side to the user side as detected by the laser detection means.

2. The active Laser Protection System device of claim 1 wherein the activated liquid crystal display prevents the laser light detected by the laser detection means from passing from the laser exposed side to the user side of the liquid crystal display.

3. The active Laser Protection System device of claim 2 wherein the microprocessor causes the liquid crystal display to display on the user side in a readable text format information regarding the laser light detected by the laser detection means.

4. The active Laser Protection System device of claim 2 wherein the liquid crystal display further comprises at least one lens of an eyeglasses.

5. The active Laser Protection System device of claim 4 wherein the microprocessor causes the liquid crystal display to display on the user side in a readable text format information regarding the laser light detected by the laser detection means.

6. The active Laser Protection System device of claim 4 wherein the microprocessor causes the liquid crystal display to display on the user side any visible non-laser light that was prevented from passing from the laser exposed side to the user side of the same wavelength as the laser light that was prevented from passing from the laser exposed side to the user side as detected by the laser detection means.

7. The active Laser Protection System device of claim 2 wherein the liquid crystal display further comprises at least one contact lens.

8. The active Laser Protection System device of claim 7 wherein the microprocessor causes the liquid crystal display to display on the user side in a readable text format information regarding the laser light detected by the laser detection means.

9. The active Laser Protection System device of claim 7 wherein the microprocessor causes the liquid crystal display to display on the user side any visible non-laser light that was prevented from passing from the laser exposed side to the user side of the same wavelength as the laser light that was prevented from passing from the laser exposed side to the user side as detected by the laser detection means.

10. The active Laser Protection System device of claim 2 wherein the liquid crystal display further comprises a window.

11. The active Laser Protection System device of claim 10 wherein the microprocessor causes the liquid crystal display to display on the user side in a readable text format information regarding the laser light detected by the laser detection means.

12. The active Laser Protection System device of claim 10 wherein the microprocessor causes the liquid crystal display to display on the user side any visible non-laser light that was prevented from passing from the laser exposed side to the user side of the same wavelength as the laser light that was prevented from passing from the laser exposed side to the user side as detected by the laser detection means.

13. The active Laser Protection System device of claim 2 wherein the liquid crystal display further comprises a windshield.

14. The active Laser Protection System device of claim 13 wherein the microprocessor causes the liquid crystal display to display on the user side in a readable text format information regarding the laser light detected by the laser detection means.

15. The active Laser Protection System device of claim 14 wherein the microprocessor causes the liquid crystal display to display on the user side any visible non-laser light that was prevented from passing from the laser exposed side to the user side of the same wavelength as the laser light that was prevented from passing from the laser exposed side to the user side as detected by the laser detection means.

16. The active Laser Protection System device of claim 1 wherein the laser detection communication means and the liquid crystal display communication means are each comprised of electrical conductors.

17. The active Laser Protection System device of claim 1 wherein the laser detection communication means and the liquid crystal display communication means are each comprised of at least one transmitter and at least one receiver.

* * * * *